US008252024B2

(12) United States Patent
Bax

(10) Patent No.: US 8,252,024 B2
(45) Date of Patent: Aug. 28, 2012

(54) SPINAL SUPPORT DEVICE

(76) Inventor: Marie-Jose Bax, Marina Del Rey, CA (US)

( * ) Notice: Subject to any disclaimer, the term of this patent is extended or adjusted under 35 U.S.C. 154(b) by 833 days.

(21) Appl. No.: 12/094,369

(22) PCT Filed: Nov. 21, 2006

(86) PCT No.: PCT/US2006/045082

§ 371 (c)(1), (2), (4) Date: Mar. 18, 2009

(87) PCT Pub. No.: WO2007/059358

PCT Pub. Date: May 24, 2007

(65) Prior Publication Data

US 2009/0306713 A1 Dec. 10, 2009

Related U.S. Application Data

(60) Provisional application No. 60/738,750, filed on Nov. 21, 2005.

(51) Int. Cl.
*A61F 5/00* (2006.01)

(52) U.S. Cl. .......................................... 606/240; 5/630

(58) Field of Classification Search .................... 601/84, 601/134; 606/237, 240; 5/630, 633, 636, 5/646, 648, 652, 654, 655.4, 657; 128/845; D24/21, 215

See application file for complete search history.

(56) References Cited

U.S. PATENT DOCUMENTS

| | | | | | |
|---|---|---|---|---|---|
| 1,250,392 | A | * | 12/1917 | Vance | 607/108 |
| 4,230,099 | A | * | 10/1980 | Richardson | 606/240 |
| D299,169 | S | * | 12/1988 | Hall | D24/215 |
| 5,279,310 | A | * | 1/1994 | Hsien | 5/632 |
| 5,467,490 | A | * | 11/1995 | Rice | 5/636 |
| 5,577,995 | A | | 11/1996 | Walker | |
| 6,425,399 | B1 | | 7/2002 | Hoster, Jr. | |

FOREIGN PATENT DOCUMENTS

| | | |
|---|---|---|
| AU | 2003/200803 | 9/2003 |
| WO | WO02/094170 | 11/2002 |

OTHER PUBLICATIONS

International Search Report and Written Opinion from corresponding International Application No. PCT/US2006/045082.

* cited by examiner

*Primary Examiner* — Quang D Thanh
(74) *Attorney, Agent, or Firm* — Greenberg Traurig, LLP

(57) ABSTRACT

A spinal support device for providing a guide to a user lying with the user's back on a surface for positioning the user's spine correctly over the surface. The device includes an elongated guide body having a first tubular portion, a second portion, and a third tubular portion parallel to the first tubular portion, wherein the first and third tubular portions are at least partially filled with a filler material such that the second portion forms a gutter or trough between the first and third tubular portions of the guide body.

20 Claims, 1 Drawing Sheet

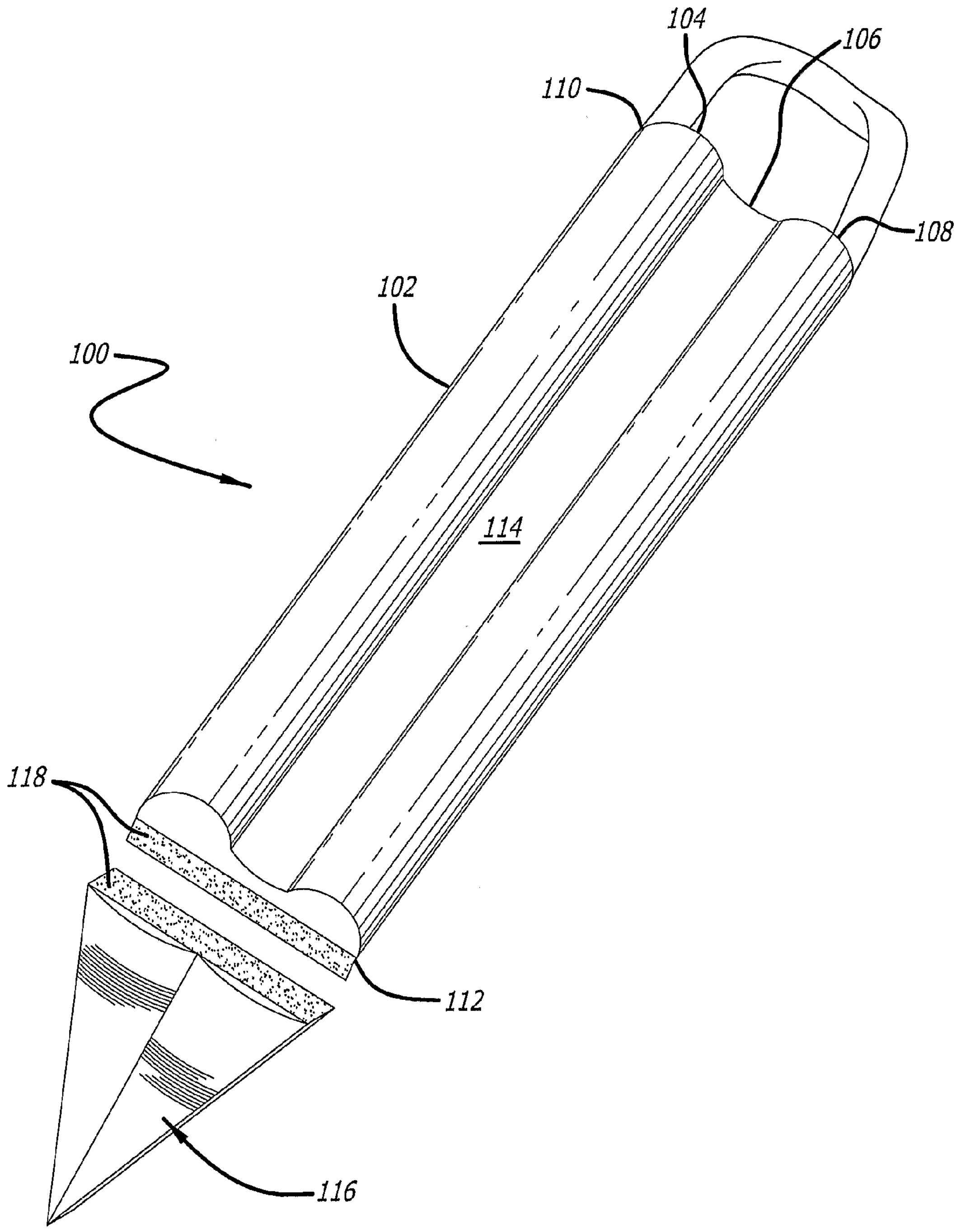
104
106
110
108
102
100
114
118
112
116

SPINAL SUPPORT DEVICE

CROSS-REFERENCE TO RELATED APPLICATIONS

This application is a U.S. national stage filing under 35 U.S.C. 371 of International Application No: PCT/US2006/045082, filed on Nov. 21, 2006, which claims the benefit of U.S. Application No. 60/738,750, filed on Nov. 21, 2005. The entire teachings of the referenced applications are incorporated herein by reference.

FIELD OF THE DISCLOSURE

This application is directed generally to physical therapy devices and more particularly to a flexible body alignment aid specifically designed for use in spinal alignment and spinal positioning awareness development.

BACKGROUND

Working with different bodies in a movement analysis and physical therapy setting requires unique approaches for assisting each individual achieve a heightened awareness of spinal alignment. This awareness then is used improve and facilitate optimal movement and mobility of the spine and whole body. However, there is a need for an aid that a user can use herself or himself to aid in sensing in their own bodies when and if a proper spinal alignment has been achieved.

SUMMARY OF THE DISCLOSURE

A spinal support device in accordance with the present disclosure provides a tactile feedback to a user of the device. The device is preferably used by a person performing various exercises or movements, preferably while at least partially reclined or sitting on a mat or other relatively cushioned flat surface. The device is preferably used to provide sensory feedback to the user of his or her spine position. The device also provides the spine with extra support and guidance where precision positioning is required, for example, in exercises associated with body core stabilization techniques. The device is particularly useful in Pilates mat exercises, exercises performed on the Pilates trapeze table, ladder barrel and spine corrector as a facilitative and alignment correction aid. The support device may also be useful for use by a person in meditative rest positions to provide added support for the back and spine.

More particularly, a spinal support device provides, or acts as, a guide to a user, for example, when lying with the user's back on a surface. The device aids the user in sensing positioning of the user's spine correctly over the surface. This device preferably includes an elongated guide body having a first tubular portion, a second portion, and a third tubular portion parallel to the first tubular portion, wherein the first and third tubular portions are at least partially filled with a filler material such as a granular material so that the second portion forms a gutter or trough between the first and third tubular portions of the guide body. The user positions the tubular portions on opposite sides of her back as she reclines on the surface. Her spine then fits into the trough formed between the two tubular portions while the tubular portions provide a tactile feedback to the user of the positioning of the tubular portions.

Preferably the portions are of equal length and about the length of the user's torso from hip to the back of the head, thus extending fully along the user's spine. Preferably the tubular portions each have a diameter of between one and two inches when partially filled with granular material, such that the user can substantively feel the pressure from the tubular portions on either side of the user's spine, and can thus help tactily feel when the user's spine is off axis. This tactile feedback is fundamental to the proper use of the device. Preferably the device is made of a soft cloth such as a cotton duck cloth for durability and may have a fabric strip handle at each end for a user to grasp.

The device may also be accompanied by a generally triangular granular filled pad that can be removably attached and detached from one end of the device. This triangular pad is designed to be placed under the user's sacrum to hold one end of the device stationary while the other end of the device is held by the users hands behind the user's head while reclining onto a surface.

Thus, one or both ends of the device may include a strip of hook and loop fastener fabric affixed thereto. The base of the triangular pad has a complementary strip of hook and loop fastener fabric affixed along the base edge. Alternatively the pad and tubular device may be fastened together by other known means such as releasable snaps.

Further features objects and advantages of the present disclosure will become more apparent from a reading of the following detailed description when taken in conjunction with the drawing and appended claims.

DRAWINGS

FIG. 1 is an exploded perspective view of the support device in accordance with the present disclosure.

DETAILED DESCRIPTION

The device 100 shown in FIG. 1 includes a spinal guide body 102 that has a first, second and third elongated parallel tubular portions 104, 106, 108 made of a flexible material such as a soft cotton duck fabric. Other fabrics may be used such as polyester or nylon fabric, but cotton is preferred. The first and third tubular portions 104 and 108 are filled with a granular filler material such as rice, buckwheat, or plastic beads and may advantageously include an aromatherapy material such as Lavender or Rosemary. The guide body 102 is preferably about the length of a person's spine, e.g. about 24-36 inches long, but could be as short as 16 inches for small users. The guide body 102 and is closed at an upper end 110 and at a bottom end 112. The second portion 106 may be have a smaller volume of a finer filler material or nothing at all such that the first and third portions 104 and 108 may be spaced apart up to about an inch, and more preferably about a quarter of an inch, when the device 100 is laid on a flat surface. The second portion 106 therefore separates the first and third portions 104 and 108 and forms a shallow space in between the two filled tubular portions 104 and 108 forming a shallow gutter or trough 114. Although not shown in FIG. 1, each end 110 and 112 may have a loop or strip of material fastened thereto to form a handle or grip for a user to grasp during use.

Optionally, the device 100 may include a generally triangular pad or cushion 116 of flexible material, also filled with a granular filler material, and preferably separated into two side by side filled portions, that may be removably fastened to the bottom end 112 of the guide body 102 via snaps or hook and loop fastener fabric 118 sewn to the bottom end 112 of the guide body 102 and along one edge of the triangular cushion 116. This cushion 116 is designed to support the user's sacrum and is preferably also lightly filled with buckwheat and Lavender or other granular material. The cushion 116 preferably has an generally isosceles triangular shape when viewed from above, although other shapes are contemplated as within the scope of the disclosure. For example, the cushion 116 may have its bottom end shaped complementary to that of bottom end 112, and its opposite end rounded or pointed as shown in FIG. 1.

The filler material in the device 100 preferably includes Lavender or Rosemary and is advantageous for its aromatherapy effects. The flexible material forming the guide body 102 and the cushion 116 is preferably a woven material such as cotton duck or synthetic canvas material that is durable but soft feel for contact with a person's back.

While the apparatus has been described in terms of what are presently considered to be the most practical and preferred embodiments, it is to be understood that the disclosure need not be limited to the disclosed embodiments. For example, the shape of the guide body 100 may be modified in diameter rather than each tubular portion having a uniform or constant diameter. Snaps may be used to removably attach the cushion 116 to the guide body 102. The filler material could optionally be a liquid or a gel rather than granular material, although a granular material is presently preferred. In embodiments in which a liquid or gel filler material is used, the outer material may be an impermeable material or the liquid or gel filler material may be in bladders that fit within the fabric material that touches a user's body. It is therefore intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A spinal support device for providing a guide to a user positioned with the user's back on a surface for positioning the user's spine correctly over the surface, the device comprising:

an elongated flexible guide body having a first tubular portion, a second portion, and a third tubular portion parallel to the first tubular portion, wherein the first and third tubular portions are at least partially filled with a flowable filler material such that the second portion forms a gutter between the first and third tubular portions of the guide body; and a triangular flexible body at one end of said elongated guide body.

2. The device according to claim 1 wherein said portions are of equal length.

3. The device according to claim 1 wherein the length of each of said portions is selected by a user to be at least equal to the distance from the user's hips to the user's neck.

4. The device according to claim 1 wherein said tubular portions each have a diameter of between 1 and 2 inches when filled with granular material.

5. The device according to claim 1 wherein the guide body is made of cloth.

6. The device according to claim 5 wherein said portions are of equal length.

7. The device according to claim 5 wherein the length of each of said portions is selected by a user to be at least equal to the distance from the user's hips to the user's neck.

8. The device according to claim 5 wherein said tubular portions each have a diameter of between 1 and 2 inches when filled with granular material.

9. The device according to claim 5 wherein the tubular portions each have a length between 16 and 36 inches.

10. The device according to claim 9 wherein the tubular portions have a diameter of between 1 and 2 inches when filled with granular material.

11. A spinal support device for providing a guide to a user positioned with the user's back on a surface for positioning the user's spine correctly over the surface, the device comprising:

an elongated flexible guide body having a first tubular portion, a second portion, and a third tubular portion parallel to the first tubular portion, wherein the first and third tubular portions are at least partially filled with a flowable filler material such that the second portion forms a gutter between the first and third tubular portions of the guide body; and a triangular flexible body removably fastened to one end of said elongated guide body.

12. The device according to claim 11 further comprising a fabric hand grip fastened to an opposite end of said elongated guide body.

13. The device according to claim 11 wherein the triangular body is fastened to the guide body via strips of complementary hook and loop fabric.

14. The device according to claim 11 wherein said tubular portions each have a diameter of between 1 and 2 inches when filled with granular material.

15. The device according to claim 11 wherein the guide body is made of cloth.

16. The device according to claim 15 wherein said portions are of equal length.

17. The device according to claim 15 wherein the length of each of said portions is selected by a user to be at least equal to the distance from the user's hips to the user's neck.

18. The device according to claim 15 wherein said tubular portions each have a diameter of between 1 and 2 inches when filled with granular material.

19. The device according to claim 15 wherein the tubular portions each have a length between 16 and 36 inches.

20. The device according to claim 19 wherein the tubular portions have a diameter of between 1 and 2 inches when filled with granular material.

* * * * *